US00PP09497P

United States Patent [19]

Imazio

[11] Patent Number: Plant 9,497

[45] Date of Patent: Apr. 9, 1996

[54] HEATH PLANT NAMED 'HAPPY II'

[75] Inventor: Bruno L. Imazio, Watsonville, Calif.

[73] Assignee: Bay City Flower Company, Half Moon Bay, Calif.

[21] Appl. No.: 361,631

[22] Filed: Dec. 22, 1994

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—James R. Cypher

[57] ABSTRACT

The present invention relates to a new and distinct variety of heath plant named *Erica persoluta* 'Happy II', a seedling of unknown pollen and seed parentage, discovered in a field of *Erica persoluta* 'Sunset', which is distinguished from *Erica persoluta* 'Happy' and all other varieties known to me by its ease of propagation, its resistance to root diseases, and the color of its flower.

1 Drawing Sheet

BACKGROUND OF THE INVENTION

This invention relates to a new and distinct variety of the Ericaceae family, named *Erica persoluta* 'Happy II' by the assignee of the invention. This new and heather variety was discovered by the inventor as a seedling of unknown pollen and seed parentage growing in a cultivated field of *Erica persoluta* 'Sunset' U.S. Plant Pat. No. 5,336. The new variety possesses the naturally compact growth habit of *Erica persoluta* 'Sunset', but was noticed because of its early and prolonged flowering habit. In this respect it is very similar to the patented plant variety *Erica persoluta* 'Happy'—U.S. Plant Pat. No. 8,650; Bruno Imazio, inventor; Bay City Flower Co., Inc. assignee.

The new variety is particularly suitable for potted plant culture because of the ease and speed with which cuttings take root and its resistance to root diseases.

The distinguishing characteristics of the new variety which differentiate it from *Erica persoluta* 'Happy' and other varieties known to me are:

1. ease of propagation,
2. resistance to root diseases, and,
3. color of the flower.

| Characteristic | 'Happy' | 'Happy II' |
|---|---|---|
| Ease of Propagation | Average | Above Average |
| Disease Resistance | Good | Very good; resistant to the root diseases Pythium and Rhizoctonia. |
| Bloom Color | R.H.S. 78 B–78 C | R.H.S. 72 B |

Since the inventor's discovery of the new variety several years ago, in a commercial nursery in the Sunset Beach area of Watsonville, Calif., the assignee, under the direction and control of the inventor at a commercial nursery in Half Moon Bay, Calif., has asexually reproduced the new cultivar through successive generations by means of cuttings and has found that its distinguishing characteristics remain true from generation to generation and appear to be firmly fixed. Those characteristics are: ease of propagation, disease resistance and bloom color.

BRIEF DESCRIPTION OF THE DRAWING

The accompanying drawings consist of color photographs that show the typical potted plant form, including the inflorescence and foliage. The colors are represented as truly as possible using conventional photographic procedures.

DETAILED DESCRIPTION OF THE NEW VARIETY

Figure 1:
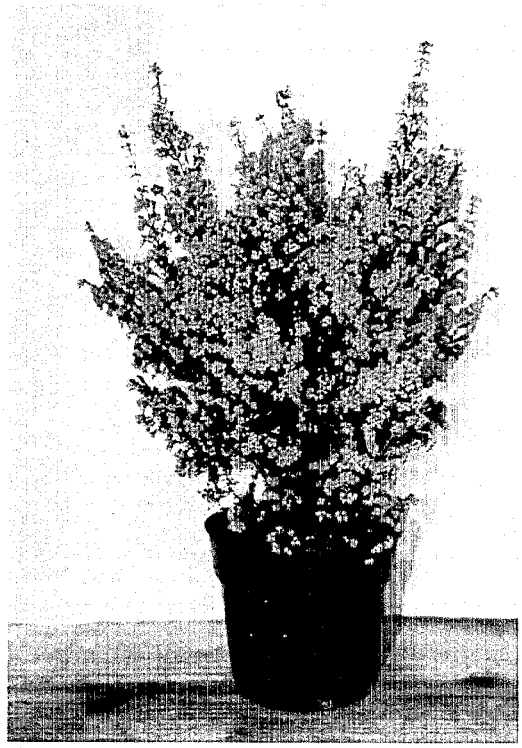
FIG. 1 is a color photograph of a potted plant of the new variety illustrating the overall form and appearance of the plant in full bloom.
Figure 2:
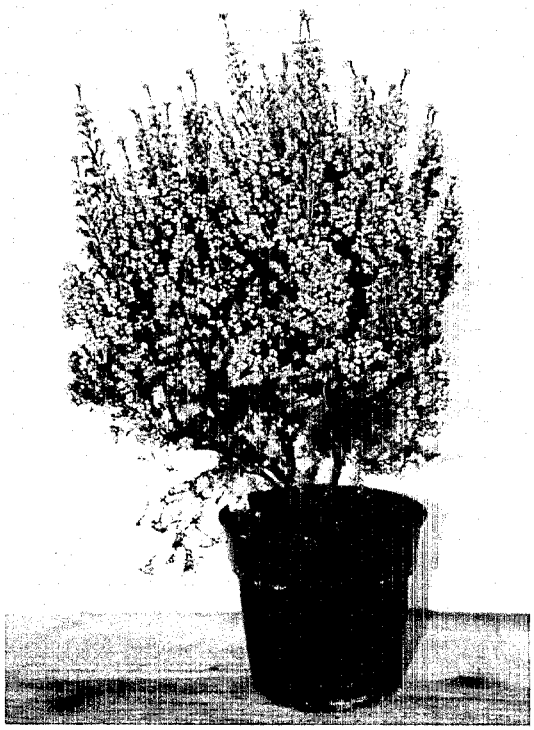
FIG. 2 is a color photograph of a potted plant of the new variety just prior to the blooms opening.
Figure 3:
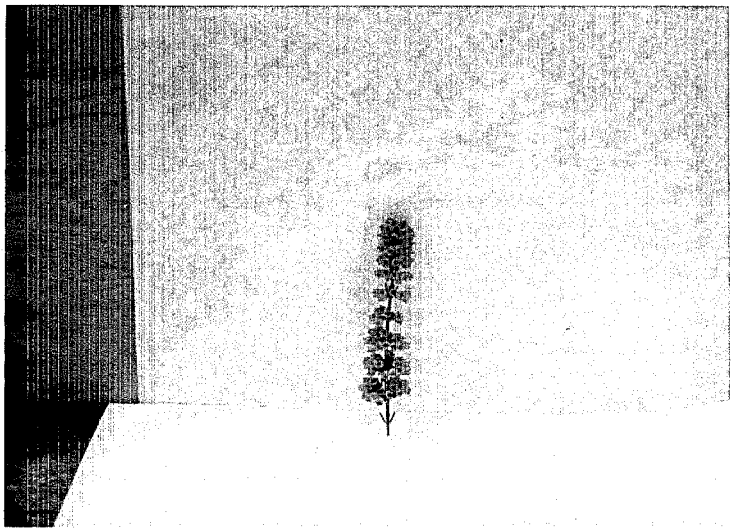
FIG. 3 is a color photograph of the open blooms.

The following is a detailed description of the new variety with color designations made according to The Royal Horticultural Society (R.H.S.) Colour Chart, published in London, England. The following description is based on observations of optimally fertilized plants in 4" pots. The plants are 14 months of age from initial propagation and were grown outside under saran in a commercial nursery in Half Moon Bay, Calif., where the average day and night temperatures are 65 degrees F. and 55 degrees F. respectively in the summer and 55 degrees F. and 45 degrees F. respectively in the winter.

The Plant

Origin: Seedling.

Parentage:

*Seed parent.*—Unknown.

*Pollen parent.*—Unknown.

Classification:

*Botanic.*—*Erica persoluta* 'Happy II.'

*Commercial.13* Happy II.

Form: Perennial, compact woody shrub.

Shape: Upright growth habit.

Height: 25.40 cm to 30.48 cm with an average of 26.04 cm for 14 month plants in 10 cm pots.

Girth: Circumference of 14 month plants in 10 cm pots is 48.26 cm to 55.88 cm.

Diameter: Actual and average diameter of 9".

Branching: Good with minimal pruning.

Growth: Naturally compact; stems become woody with age; stems strong and flexible.

Foliage: Abundant, plant covered with small needle-like leaves.

*Size of leaf.*—4 mm Long by 1 mm wide.

*Shape of leaf.*—Acerose like, convexed.

*Character.*—Sulcate.

*Color.*—R.H.S. 144 A.

*Texture.*—Smooth.

Hardiness: Can tolerate temperatures from 28 to 100 degrees F.

The Bud

Size: Fully developed.
*Length.*—3 mm.
*width.*—2 mm.
*Diameter.*—2 mm.
Color: R.H.S. 27 C.
Rate of opening: Rapid, commencing at the base of the inflorescence and progressing continuously to the tip.
Petals: Corroline flowers with inconspicuous sepals; R.H.S. 71 A.

Inflorescence

Blooming habit: Annually, early October through December.
Size of bloom: 4 mm long by 2 mm wide.
Flowering habit: Primarily in axiallary verticils and on short branches from the rachis, forming a vertical spike-like, paniculate raceme. Short branches terminate in single cluster from 1 to 6 or more flowers.
Shape: Urceolate.
Appearance: Santiny.
Flower color: R.H.S. 72 B.
Peduncle: The length of the peduncle will vary depending upon the orientation of the branch and the light penetration into the plant. Measurements of the peduncle ranged from 0.5 cm to 3.0 cm. Distance is measured to the first branch encountered that has flowers.
Pedicel: 2 mm.
Branch length: Usually 1.0 cm at bottom of infloresence and becoming progresively shorter travelling up the rachis.
Rachis:
*Color.*—Woody portion of rachis is R.H.S. 165 A; new growth is R.H.S. 60 A.
*Strength.*—Woody to supple; flexible.
Persistence: Blooms do not shed easily, remain long after the plant ceases to draw water.
Fragrance: Faint.

The outstanding economic and aesthetic characteristics of this new variety which distinguish it from other commercial varieties such as *Erica persoluta* 'Heidi' and 'Happy' are: flower color, resistance to root diseases and ease of asexual propagation.

| | 'HEIDI' | 'HAPPY' | 'HAPPY II' |
|---|---|---|---|
| The Plant | | | |
| Height | A 4" pot will produce a plant 8" to 9" high in 18 months with little or no pruning. | A 4" pot will produce a plant 13" to 15" high in 16 months with minimal pruning. | A 4" pot will produce a plant 10" to 12" high in 16 months with minimal pruning. |
| Form | Short, dense appearing, compact woody shrub. | Same | Same |
| Shape | Upright, stems curving slightly to accommodate the fullness of the plant. | Upright, stems curving slightly to accommodate the fullness of the plant. | Same |
| Branch-ing | Naturally generous, minimal or no pruning needed. | Ample, minimal prunings (1–2) necessary to encourage branching. | Same |
| Growth | Upright but naturally short and branching with woody flexible strength. | Same | Same |
| Blooming Season | Annual, mid Jan. to mid Feb. | Annual, early Oct. to mid. Jan. | Annual, early Oct. to the end of Dec. |
| Ease of Propaga-tion | Average | Average | Above average |
| Disease Resist-ance | Average | Good | Very good. Resistant to the root diseases Pythium and Rhizoctonia. |
| Foliage | | | |
| Color | R.H.S. 143 A | R.H.S. 144 A | R.H.S. 144 A |
| Size | 3 mm | Same | 4 mm long, 1 mm wide |
| Shape | Spike-like with stiff erect stems and acerose leaves | Same | Same |
| Quantity | Abundant | Same | Same |
| Bloom | | | |
| Size | 3 mm × 1.5 mm | 3 mm × 2.5 mm | 4 mm × 2 mm |
| Borne | In clusters with terminal buds. | Same | Same |
| Shape | Urceolate | Same | Same |
| Color | R.H.S. 71C–71D | R.H.S 78B–78C | R.H.S. 72 B |
| Rate of Opening | Rapid, pro-gressive and continuous beginning at base of stem and progressing to tip. | Same | Same |

I claim:

1. A new and distinct hybrid plant variety of the Heath family substantially as herein shown and described.

* * * * *